United States Patent [19] [11] 4,359,460
Nair et al. [45] Nov. 16, 1982

[54] 6'-(1-ADAMANTANECARBOXYLATE)-6-O-α-D-GALACTOPYRANOSYL-α-D-GLUCOPYRANOSE SULFATE SALTS

[75] Inventors: Vijay G. Nair, Piermont; Seymour Bernstein, New City, both of N.Y.

[73] Assignee: American Cyanamid Company, Stamford, Conn.

[21] Appl. No.: 310,672

[22] Filed: Oct. 13, 1981

[51] Int. Cl.³ ............... A61K 31/715; A61K 31/73; C07H 5/08
[52] U.S. Cl. .................. 424/180; 536/18.7; 536/55.1; 536/118; 536/122; 536/123; 536/124
[58] Field of Search .......... 424/180; 536/4, 118, 536/119, 18, 54, 55

[56] References Cited

U.S. PATENT DOCUMENTS

| 3,023,183 | 2/1962 | Nelson | 536/118 |
| 3,356,674 | 12/1967 | Ikeda et al. | 536/4 |
| 4,021,544 | 5/1977 | Nair et al. | 536/118 |
| 4,021,545 | 5/1977 | Nair et al. | 536/118 |
| 4,232,150 | 11/1980 | Nair et al. | 536/119 |

Primary Examiner—Johnnie R. Brown
Attorney, Agent, or Firm—Anne M. Rosenblum

[57] ABSTRACT

6'-(1-Adamantanecarboxylate)-6-O-α-D-galactopyranosyl-α-D-glucopyranose sulfate salts, useful as complement inhibitors, and the process for making such compounds.

13 Claims, No Drawings

6'-(1-ADAMANTANECARBOXYLATE)-6-O-α-D-GALACTOPYRANOSYL-α-D-GLUCOPYRANOSE SULFATE SALTS

BACKGROUND OF THE INVENTION

1. Field of Invention

The present invention relates to novel 6'-(1-adamantanecarboxylate)-6-O-α-D-galactopyranosyl-α-D-glucopyranose sulfate salts and their use as inhibitors of the complement system of warm-blooded animals. The invention further concerns a process for making such compounds.

2. Description of the Prior Art

The term "complement" refers to a complex group of proteins in body fluids that, working together with antibodies or other factors, play an important role as mediators of immune, allergic, immunochemical and/or immunopathological reactions. The reactions in which complement participates take place in blood serum or in other body fluids, and hence are considered to be humoral reactions.

With regard to human blood, there are at present more than 20 proteins in the complement system consisting of the so-called classical and alternative pathways. These complement proteins are generally designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its biochemical, biological and pathological role in the body processes can be found in, for example, Bull. W.H.O. 39: 935 (1968); Annu. Rev. Med. 19: 1 (1968); Johns Hopkins Med. J. 128: 57 (1971); Harvey Lect. 66: 75 (1972); N. Engl. J. Med. 287: 452, 489, 454, 592, 642 (1972); Sci. Am. 229 (5): 54 (1973); Fed. Proc. 32: 134 (1973); Med. World, Oct. 11, 1974, p. 53; J. Allergy Clin. Immunol. 53: 298 (1974); Cold Spring Harbor Conf. Cell Proliferation 2/Proteases Biol. Control: 229 (1975); Annu. Rev. Biochem. 44: 697 (1975); Complement in Clinical Medicine, Dis. Mon. (1975); Complement, Scope, December 1975; Ann. Intern. Med. 84: 580 (1976); Transplant Rev.: 32 (1976); "Complement: Mechanisms and Functions," Prentice-Hall, Englewood Cliffs, N.J. (1976); Essays Med. Biochem. 2: 1 (1976); Hosp. Pract. 12: 33 (1977); Perturbation of Complement in Disease, Chap. 15 in Biol. Amplification Systems in Immunol. (Ed. Day and Good), Plenum, N.Y. and London (1977); Am. J. Clin. Pathol. 68: 647 (1977); Biochem. Soc. Trans. 5: 1659 (1977); Harvey Lect. 72: 139 (1976–1977); J. Periodontol. 48: 505 (1977); Biochem. Soc. Trans. 6: 798 (1978); Clin. and Exp. Dermatol. 4: 271 (1979); Infect. Dis. Rev. 1: 483 (1979).

The complement system (e.g., classical pathway) can be considered to consist of three subsystems: (1) a recognition unit (C1q) which enables it to combine with antibody molecules that have detected a foreign invader; (2) an activation unit (C1r, C1s, C2, C4, C3) which prepares a site on the neighboring membrane; and (3) an attack unit (C5, C6, C7, C8 and C9) which creates a "hole" in the membrane. The membrane attack unit is nonspecific; it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to host's cells. Immunity is, therefore, a double-edged sword.

Activation of the complement system also accelerates blood clotting. This action comes about by way of the complement-mediated release of a clotting factor from platelets. The biologically active complement fragments and complexes become involved in reactions that damage the host's cells. These pathogenic reactions can result in the development of immune-complex diseases. For example, in some forms of nephritis, complement damages the basal membrane of the kidney, resulting in the escape of protein from the blood into the urine. The disease disseminated lupus erythematosus belongs in this category; its symptoms include nephritis, visceral lesions and skin eruptions. The treatment of diphtheria or tetanus with the injection of large amounts of antitoxin sometimes results in serum sickness, an immune-complex disease. Rheumatoid arthritis also involves immune complexes. Like disseminated lupus erythematosus, it is an autoimmune disease in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection it also results in inflammation and tissue damage in the immunopathological process. The nature of certain complement proteins, suggestion regarding the mode of complement binding to biological membranes and the manner in which complement effects membrane damage are discussed in Annu. Rev. Biochem. 38: 389 (1969); J. Exp. Med. 141: 724 (1975); J. Immunol. 116: 1431 (1976); 119: 1, 1195, 1358, 1482 (1977); 120: 1841 (1978); Immunochemistry 15: 813 (1978); J. Biol. Chem. 254: 9908 (1979).

A variety of substances have been disclosed as inhibiting the complement system, i.e., as complement inhibitors. For example, the compounds 3,3'-ureylenebis[6-(2-amino-8-hydroxy-6-sulfo-1-naphthylazo)benzenesulfonic acid], tetrasodium salt (chlorazol fast pink), heparin and a sulphated dextran have been reported to have an anti-complementary effect, Br. J. Exp. Pathol. 33: 327 (1952). German Pat. No. 2,254,893 or South African Pat. No. 727,923 discloses certain 1-(diphenylmethyl)-4-(3-phenylallyl)piperazines useful as complement inhibitors. Other chemical compounds having complement inhibiting activity are disclosed in, for example, J. Med. Chem. 12: 415, 902, 1049, 1053 (1969); Can. J. Biochem. 47: 547 (1969); J. Immunol. 104: 279 (1970); J. Immunol. 106: 241 (1971); J. Immunol. 111: 1061 (1973); Biochim. Biophys. Acta 317: 539 (1973); Life Sci. 13: 351 (1973); J. Immunol. 113: 584 (1974); Immunology 26: 819 (1974); J. Med. Chem. 17: 1160 (1974); Biochim. Biophys. Res. Comm. 67: 225 (1975); Ann. N.Y. Acad. Sci. 256: 441 (1975); J. Med. Chem. 19: 634, 1079 (1976); J. Immunol. 118: 466 (1977); Arch. Int. Pharmacodyn. 226: 281 (1977); Biochem. Pharmacol. 26: 325 (1977); J. Pharm. Sci. 66: 1367 (1977); Chem. Pharm. Bull. 25: 1202 (1977); Biochim. Biophys. Acta 484: 417 (1977); J. Clin. Microbiol. 5: 278 (1977); Immunochemistry 15: 231 (1978); Immunology 34: 509 (1978); J. Exp. Med. 147: 409 (1978); Thromb. Res. 14: 179 (1979); J. Immunol. 122: 2418 (1979); J. Chem. Soc. Chem. Comm. 726 (1979); Immunology 36: 131 (1979); Biochim. Biophys. Acta 611: 196 (1980); and J. Med. Chem. 23: 240 (1980).

It has been reported that the known complement inhibitors, epsilon-aminocaproic acid and tranexamic acid, have been used with success in the treatment of hereditary angioneurotic edema, a disease state resulting from an inherited deficiency or lack of function of the serum inhibitor of the activated first component of complement (C1 inhibitor), N. Engl. J. Med. 286: 808 (1972); 287: 452 (1972); Ann. Intern. Med. 84: 580 (1976); J. Allergy Clin. Immunol. 60: 38 (1977). Also androgenic steroids have been used successfully in the treatment of this physiological disorder; see Medicine 58: 321 (1979); Arthritis Rheum. 22: 1295 (1979); Am. J. Med. 66: 681 (1979); and J. Allergy Clin. Immunol. 65: 75 (1980).

It has also been reported that the drug pentosanpolysulfoester has an anticomplementary activity on human serum, both in vitro and in vivo, as judged by the reduction in total hemolytic complement activity, Pathol. Biol. 25: 33; 25 (2): 105; 25 (3): 179 (1977).

SUMMARY OF THE INVENTION

It has now been discovered that 6'-(1-adamantanecarboxylate)-6-O-α-D-galactopyranosyl-α-D-glucopyranose sulfate salts interact with the complement reaction sequence, thereby inhibiting complement activity in body fluids.

This invention also concerns a method of inhibiting the complement system in a body fluid which comprises subjecting body fluid complement to the action of an effective complement inhibiting amount of the above-identified compounds. This invention further deals with a method of inhibiting the complement system in a warm-blooded animal which comprises administering to said animal an effective complement inhibiting amount of the above described compounds.

DETAILED DESCRIPTION OF THE INVENTION

In accordance with the present invention, there are provided novel compounds represented by the following generic formula:

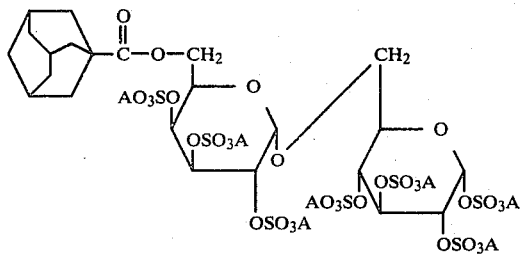

wherein A is a pharmaceutically acceptable cation salt, wherein the salt forming moiety is selected from the group consisting of alkali metal, alkaline earth metal, ammonia and substituted ammonia selected from the group consisting of trialkylamine ($C_1$–$C_6$), piperidine, pyrazine, alkanolamine ($C_2$–$C_6$) and cycloalkylamine ($C_3$–$C_6$).

Particularly preferred compounds of this invention which are of major interest as complement inhibitors are listed below.

6'-(1-Adamantanecarboxylate)-6-O-α-D-galactopyranosyl-α-D-glucopyranose, heptakis (H-sulfate), heptasalt with trimethylamine 6'-(1-Adamantanecarboxylate)-6-O-α-D-galactopyranosyl-α-D-glucopyranose, heptakis (H-sulfate), heptasodium salt.

Additionally, the instant invention involves a method of inhibiting the complement system in a body fluid, such as blood serum, which comprises subjecting body fluid complement to the action of an effective complement inhibiting amount of a compound of the above formula. Body fluids can include blood, plasma, serum, synovial fluid, cerebrospinal fluid, or pathological accumulations of fluid such as pleural effusion, etc. This invention further concerns a method of inhibiting the complement system in a warm-blooded animal which comprises administering to said warm-blooded animal an effective complement inhibiting amount of a compound of the above formula.

The compounds of the present invention find utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of autoallergic hemolytic anemia, certain kinds of platelet disorders and certain kinds of vasculitis. These compounds may also be used in the therapeutic treatment of warm-blooded animals having non-immunologic diseases such as paroxysmal nocturnal hemoglobinurea, hereditary angioneurotic edema (such as Suramin Sodium, etc.) and inflammatory states induced by the action of bacterial or lysosomal enzymes on the appropriate complement components as, for example, inflammation following coronary occlusion. They may also be useful in the treatment of transplant rejection and ulcers and as blood culture and transport mediums.

In addition the following compounds are of interest as intermediates in the preparation of the above compounds.

6'-(1-Adamantanecarboxylate)-6-O-α-D-galactopyranosyl-α-D-glucopyranose

6'-(1-Adamantanecarboxylate)-6-O-α-D-galactopyranosyl-α-D-glucopyranose, heptaacetate.

The compounds of the present invention may be prepared according to the following flowchart.

FLOWCHART

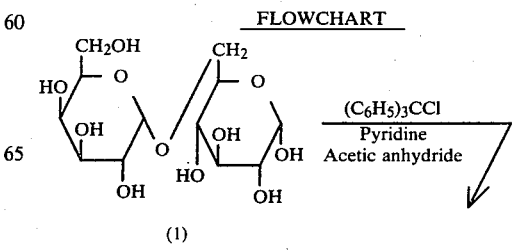

(1)

-continued
FLOWCHART

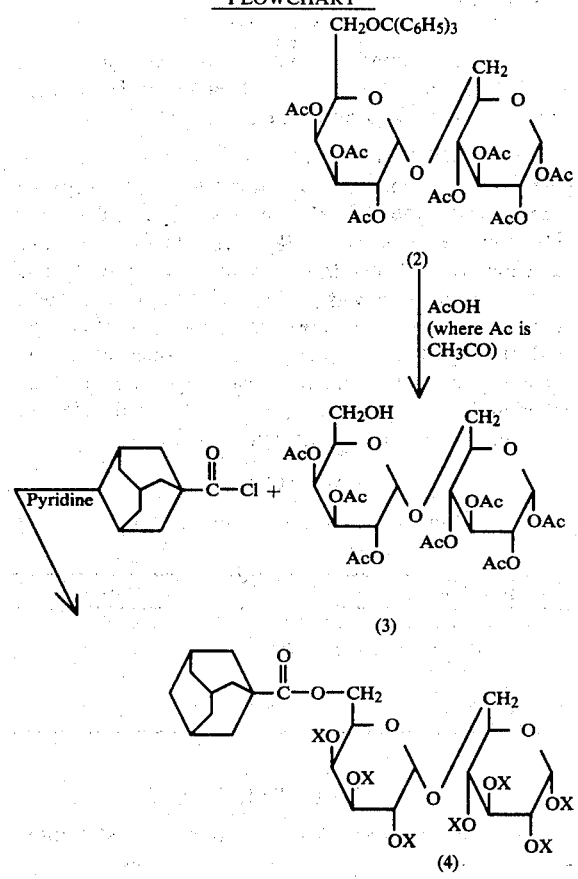

In accordance with the above reaction scheme, 6-O-α-D-galactopyranosyl-α-D-glucopyranose (1) is suspended in pyridine, calcium sulfate is added and the mixture is heated at 75°–100° C. for 15 to 60 minutes. Trityl chloride is added and the mixture is heated and stirred for several hours, then cooled. Acetic anhydride is added and after standing for several hours the solid 6-O-(6-O-trityl-α-D-galactopyranosyl)-α-D-glucopyranose, heptaacetate (2) is collected. The trityl compound (2) is heated with glacial acetic acid at 40°–70° C. for several hours then cooled and extracted with dichloromethane. The organic extracts are evaporated to a glass which is purified by silica gel column chromatography, using the system ethyl acetate:hexane (1:1) giving 6-O-α-D-galactopyranosyl-α-D-glucopyranose, heptaacetate (3). The heptaacetate (3) in pyridine is treated with 1-adamantyl chloride with stirring for several hours, then poured into ice giving 6'-(1-adamantanecarboxylate)-6-O-α-D-galactopyranosyl-α-D-glucopyranose, heptaacetate (4) where

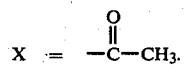

The compound (4) where

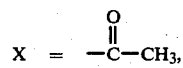

is dissolved in methanol:water:triethylamine (6:2:3), stirred for several hours and evaporated giving 6'-(1-adamantanecarboxylate)-6-O-α-D-galactopyranosyl-α-D-glucopyranose (4) where X=OH. This sugar (4), where X=OH, is added to a mixture of trimethylamine-sulfur trioxide in dimethylformamide and stirred for several hours giving 6'-(1-adamantanecarboxylate)-6-O-α-D-galactopyranosyl-α-D-glucopyranose, heptakis (H-sulfate), heptasalt with trimethylamine (4) where $X = -SO_3 \cdot HN(CH_3)_3$. This trimethylamine salt is treated with 30% sodium acetate, for example, and precipitated with ethanol giving 6'-(1-adamantanecarboxylate)-6-O-α-D-galactopyranosyl-α-D-glucopyranose, heptakis (H-sulfate), heptasodium salt (4) where $X = SO_3Na$ or may be treated with a different alkali metal or alkaline earth metal cation-containing compound or ammonia or a substituted ammonia selected from the group consisting of trialkylamine ($C_1$–$C_6$), piperidine, pyrazine, alkanolamine ($C_2$–$C_6$) and cycloalkylamine ($C_3$–$C_6$).

It is generally preferred that the respective product of each process step, described hereinabove, is separated and/or isolated prior to its use as starting material for subsequent steps. Separation and isolation can be effected by any suitable purification procedure such as, for example, evaporation, crystallization, column chromatography, thin-layer chromatography, distillation, etc. Also, it should be appreciated that when typical reaction conditions (e.g., temperatures, mole ratios, reaction times) have been given, the conditions which are both above and below these specified ranges can also be used, though generally less conveniently.

The term "pharmaceutically acceptable salts" refers to those salts of the parent compound which do not significantly or adversely affect the pharmaceutical properties (e.g., toxicity, effectiveness, etc.) of the parent compound. The salt forming moiety of the present invention which is pharmaceutically acceptable includes the alkali metals (e.g., sodium, potassium, etc.); alkaline earth metals (e.g., calcium, etc.); ammonia; and substituted ammonia selected from the group consisting of trialkylamine ($C_1$–$C_6$), piperidine, pyrazine, alkanolamine ($C_2$–$C_6$) and cycloalkylamine ($C_3$–$C_6$).

The term "trialkylamine ($C_1$–$C_6$)" defines those amines having three aliphatic fully saturated hydrocarbon substituents containing 1 to 6 carbon atoms either linearly or branched. Typically, these amines are trimethylamine, triethylamine, tripropylamine, dimethylethylamine, dimethyl-1-propylamine, etc. The term "alkanolamine ($C_2$–$C_6$)" refers to the above-defined trialkylamines additionally substituted with at least one and not more than three hydroxy groups on at least two of the alkyl hydrocarbon chains. Such amines are, for example, triethanolamine, tripropanolamine, etc. The term "cycloalkylamine ($C_3$–$C_6$)" is defined as the 3 to 6 fully saturated carbocyclic moieties such as cyclopropyl, methylcyclobutyl, cyclopentyl, cyclohexyl, etc.

As used hereinabove and below unless expressly stated to the contrary, all temperatures and temperature ranges refer to the centigrade system and the terms "ambient" or "room temperature" refer to about 20° C. The term "percent" or "(%)" refers to weight percent and the terms "mole" and "moles" refer to gram moles. The term "equivalent" refers to a quantity of reagent equal in moles to the moles of the preceding or succeeding reactant recited in the Preparation or Example in the term of moles of finite weight or volume.

A further understanding of the invention can be obtained from the following non-limiting Preparations and Examples.

EXAMPLE 1

6'-(1-Adamantanecarboxylate)-6-O-α-D-galactopyranosyl-α-D-glucopyranose, heptaacetate A 5.13 g portion of anhydrous 6-O-α-D-galactopyranosyl-α-D-glucopyranose is suspended in 50 ml of pyridine and 5.0 g of anhydrous calcium sulfate is added. This mixture is heated at 90° C. for 30 minutes, then 4.6 g of trityl chloride is added and heating and stirring are continued for 2 hours. The solution is cooled to room temperature, 10 ml of acetic anhydride is added and the mixture is allowed to stand overnight. The mixture is poured into crushed ice and the solid is filtered, washed with water and dried, giving 10 g of 6-O-(6-O-trityl-α-D-galactopyranosyl)-α-D-glucopyranose, heptaacetate as a colorless granular solid.

The above trityl compound is stirred with 100 ml of 70% acetic acid at 60° C. for 4 hours. The mixture is cooled, filtered and the filtrate is diluted with water, then extracted with 250 ml of dichloromethane. The organic extract is washed with water, then sodium bicarbonate solution and dried over sodium sulfate. The solvent is evaporated in vacuo, giving 7.0 g of a colorless glass which is applied to a 100 g silica gel column, prepared in ethyl acetate:hexane (1:4), and eluted first with the above solvent system, then with ethyl acetate:hexane (1:1). Eight 200 ml fractions are collected. Fractions 4-6 are combined and evaporated to dryness in vacuo, giving 3.4 g of 6-O-α-D-galactopyranosyl-α-D-glucopyranose heptaacetate.

A 3.18 g portion of the immediate preceding compound is dissolved in 25 ml of pyridine and 1.25 g of 1-adamantoyl chloride is added. This solution is stirred for 20 hours, then poured into crushed ice and the solid is filtered, washed with water and dried, giving 2.8 g of the desired product as a colorless granular solid.

EXAMPLE 2

6'-(1-Adamantanecarboxylate)-6-O-α-D-galactopyranosyl-α-D-glucopyranose

A 2.5 g portion of 6'-(1-adamantanecarboxylate)-6-O-α-D-galactopyranosyl-α-D-glucopyranose heptaacetate is dissolved in 55 ml of a mixture of methanol, water and triethylamine (6:2:3). The mixture is stirred for 24 hours, then evaporated to dryness in vacuo and the residue is redissolved in a small amount of water. This solution is treated with Amberlite ® IR-120(H+ form) resin and charcoal, then filtered through diatomaceous earth. Evaporation of the filtrate in vacuo at 58° C. gives 1.4 g of the desired product as a pale brown glass.

EXAMPLE 3

6'-(1-Adamantanecarboxylate)-6-O-α-D-galactopyranosyl-α-D-glucopyranose, heptakis ($\underline{H}$-sulfate), heptasalt with trimethylamine A mixture of 3.0 g of trimethylamine-sulfur trioxide in 40 ml of dimethylformamide is warmed to produce solution. A 750 mg portion of 6'-(1-adamantanecarboxylate)-6-O-α-D-galactopyranosyl-α-D-glucopyranose is added and the mixture is stirred for 24 hours. The gummy product is triturated with ethanol, filtered, washed with ethanol, then ether and dried in vacuo, giving 2.3 g of the desired product as a pale brown granular solid.

EXAMPLE 4

6'-(1-Adamantanecarboxylate)-6-O-α-D-galactopyranosyl-α-D-glucopyranose, heptakis ($\underline{H}$-sulfate), heptasodium salt A 2.0 g portion of 6'-(1-adamantanecarboxylate)-6-O-α-D-galactopyranosyl-α-D-glucopyranose, heptakis ($\underline{H}$-sulfate), heptasalt with trimethylamine is dissolved in water and 10 ml of 30% aqueous sodium acetate solution is added. The mixture is swirled, then allowed to stand 15 minutes and poured into 125 ml of ethanol with stirring. The resulting gum is triturated with fresh ethanol, the solid is filtered, washed with ethanol then ether and dried in vacuo, gving 1.4 g of the desired product as a pale brown granular solid.

EXAMPLE 5

Preparation of Compressed Tablet

| Ingredient | mg/Tablet |
| --- | --- |
| Active Compound | 0.5-500 |
| Dibasic Calcium Phosphate NF | qs |
| Starch USP | 40 |
| Modified Starch | 10 |
| Magnesium Stearate USP | 1-5 |

EXAMPLE 6

Preparation of Compressed Tablet—Sustained Action

| Ingredient | mg/Tablet |
| --- | --- |
| Active Compound as Aluminum Lake*, Micronized | 0.5-500 (as acid equivalent) |
| Dibasic Calcium Phosphate NF | qs |
| Alginic Acid | 20 |
| Starch USP | 35 |
| Magnesium Stearate USP | 1-10 |

*Complement inhibitor plus aluminum sulfate yields aluminum complement inhibitor. Complement inhibitor content in aluminum lake ranges from 5-30%.

EXAMPLE 7

Preparation of Hard Shell Capsule

| Ingredient | mg/Capsule |
| --- | --- |
| Active Compound | 0.5-500 |
| Lactose, Spray Dried | qs |
| Magnesium Stearate | 1-10 |

EXAMPLE 8

Preparation of Oral Liquid (Syrup)

| Ingredient | % W/V |
| --- | --- |
| Active Compound | 0.05-5 |
| Liquid Sugar | 75.0 |
| Methyl Paraben USP | 0.18 |
| Propyl Paraben USP | 0.02 |
| Flavoring Agent | qs |
| Purified Water qs ad | 100.0 |

EXAMPLE 9

Preparation of Oral Liquid (Elixir)

| Ingredient | % W/V |
|---|---|
| Active Compound | 0.05-5 |
| Alcohol USP | 12.5 |
| Glycerin USP | 45.0 |
| Syrup USP | 20.0 |
| Flavoring Agent | qs |
| Purified Water qs ad | 100.0 |

EXAMPLE 10

Preparation of Oral Suspension (Syrup)

| Ingredient | % W/V |
|---|---|
| Active Compound as Aluminum Lake, Micronized | 0.05-5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

EXAMPLE 11

Preparation of Injectable Solution

| Ingredient | % W/V |
|---|---|
| Active Compound | 0.05-5 |
| Benzyl Alcohol NF | 0.9 |
| Water for Injection | 100.0 |

EXAMPLE 12

Preparation of Injectable Oil

| Ingredient | % W/V |
|---|---|
| Active Compound | 0.05-5 |
| Benzyl Alcohol | 1.5 |
| Sesame Oil qs ad | 100.0 |

EXAMPLE 13

Preparation of Intra-Articular Product

| Ingredient | Amount |
|---|---|
| Active Compound | 2-20 mg |
| NaCl (physiological saline) | 0.9% |
| Benzyl Alcohol | 0.9% |
| Sodium Carboxymethylcellulose | 1.5% |
| pH adjusted to 5.0-7.5 | |
| Water for Injection qs ad | 100% |

EXAMPLE 14

Preparation of Injectable Depo Suspension

| Ingredient | % W/V |
|---|---|
| Active Compound | 0.05-5 (acid equivalent) |
| Polysorbate 80 USP | 0.2 |
| Polyethylene Glycol 4000 USP | 3.0 |
| Sodium Chloride USP | 0.8 |
| Benzyl Alcohol NF | 0.9 |
| HCl to pH 6-8 | qs |
| Water for Injection qs ad | 100.0 |

EXAMPLE 15

Preparation of Dental Paste

| Ingredient | % W/W |
|---|---|
| Active Compound | 0.05-5 |
| Zinc Oxide | 15 |
| Polyethylene Glycol 4000 USP | 50 |
| Distilled Water qs | 100 |

EXAMPLE 16

Preparation of Dental Ointment

| Ingredient | % W/W |
|---|---|
| Active Compound | 0.05-5 |
| Petrolatum, White USP qs | 100 |

EXAMPLE 17

Preparation of Dental Cream

| Ingredient | % W/W |
|---|---|
| Active Compound | 0.05-5 |
| Mineral Oil | 50 |
| Beeswax | 15 |
| Sorbitan Monostearate | 2 |
| Polyoxyethylene 20 Sorbitan Monostearate | 3 |
| Methyl Paraben USP | 0.18 |
| Propyl Paraben USP | 0.02 |
| Distilled Water qs | 100 |

EXAMPLE 18

Preparation of Topical Cream

| Ingredient | % W/W |
|---|---|
| Active Compound | 0.05-5 |
| Sodium Lauryl Sulfate | 1 |
| Propylene Glycol | 12 |
| Stearyl Alcohol | 25 |
| Petrolatum, White USP | 25 |
| Methyl Paraben USP | 0.18 |
| Propyl Paraben USP | 0.02 |
| Purified Water qs | 100 |

EXAMPLE 19

Preparation of Topical Ointment

| Ingredient | % W/W |
|---|---|
| Active Compound | 0.05-5 |
| Cholesterol | 3 |
| Stearyl Alcohol | 3 |
| White Wax | 8 |
| Petrolatum, White USP qs | 100 |

EXAMPLE 20

Preparation of Spray Lotion (Non-aerosol)

| Ingredient | % W/W |
|---|---|
| Active Compound | 0.05-5 |
| Isopropyl Myristate | 20 |
| Alcohol (Denatured) qs | 100 |

EXAMPLE 21

Preparation of Buccal Tablet

| Ingredient | mg/Tablet |
|---|---|
| Active Ingredient | 3.25 |
| 6x Sugar | 290.60 |
| Acacia | 14.53 |
| Soluble Starch | 14.53 |
| F. D. & C. Yellow No. 6 Dye | 0.49 |
| Magnesium Stearate | 1.60 |
|  | 325.00 |

The final tablet will weigh about 325 mg and may be compressed into buccal tablets in flat faced or any other tooling shape convenient for buccal administration.

EXAMPLE 22

Preparation of Lozenge

| Ingredient | g/Lozenge |
|---|---|
| Active Ingredient | 0.0140 |
| Kompact ® Sugar (Sucrest Co.) | 0.7138 |
| 6× Sugar | 0.4802 |
| Sorbitol (USP Crystalline) | 0.1038 |
| Flavor | 0.0840 |
| Magnesium Stearate | 0.0021 |
| Dye | qs |
| Stearic Acid | 0.0021 |
|  | 1.4000 |

The ingredients are compressed into ⅝ flat based lozenge tooling. Other shapes may also be utilized.

The compounds of the present invention may be administered internally, e.g., orally, intra-articularly or parenterally, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses of the acid or salt can contain from about 0.5 mg to about 500 mg.

The compounds of the present invention may also be administered topically in the form of ointments, creams, lotions and the like, suitable for the treatment of complement dependent dermatological disorders.

Moreover, the compounds of the present invention may be administered in the form of dental pastes, ointments, buccal tablets and other compositions suitable for application periodontally for the treatment of periodontitis and related diseases of the oral cavity.

In therapeutic use, the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate nontoxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term "dosage form," as described herein, refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention is indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of the compounds of this invention has been demonstrated by one or both of the following identified tests: (i) Test Code 026 (C1 inhibitor)—This test measures the ability of activated human C1 to destroy fluid phase human C2 in the presence of C4 and appropriate dilutions of the test compound. An active inhibitor protects C2 from C1 and C4; and (ii) Cap 50 Test—Here, appropriate amounts of the test compound are added to a pool of guinea pig serum in vitro, after which the undiluted serum capillary tube assay of U.S. Pat. No. 3,876,376 is run. The concentration of compound inhibiting 50% is reported. The results of Test Code 026 appear in Table I together with results of Test Code Cap 50. Table I shows that the compounds of the invention possess highly significant complement inhibiting activity in warm-blooded animals.

TABLE 1

Biological Activities

| Compound | C1 026* Wells | Cap 50 |
| --- | --- | --- |
| 6'-(1-Adamantanecarboxylate)-6-O—α-D-galactopyranosyl-α-D-glucopyranose, heptakis (H—sulfate), heptasalt with trimethylamine | +6** | |
| 6'-(1-Adamantanecarboxylate)-6-O—α-D-galactopyranosyl-α-D-glucopyranose, heptakis (H—sulfate), heptasodium salt | +7 | 417 |

*Test identified by code herein.
**Activity in wells, a serial dilution assay; higher well number indicates higher activity.

We claim:
1. A compound selected from those of the formula:

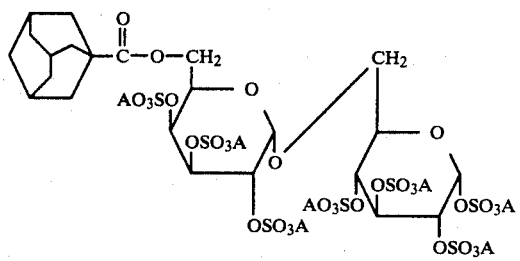

wherein A is a pharmaceutically acceptable cation salt, wherein the salt forming moiety is selected from the group consisting of alkali metal, alkaline earth metal, ammonia and substituted ammonia selected from the group consisting of trialkylamine ($C_1$–$C_6$), piperidine, pyrazine, alkanolamine ($C_2$–$C_6$) and cycloalkylamine ($C_3$–$C_6$).

2. The compound according to claim 1, 6'-(1-adamantanecarboxylate)-6-O-α-D-galactopyranosyl-α-D-glucopyranose, heptakis (H-sulfate), heptasalt with trimethylamine.

3. The compound according to claim 1, 6'-(1-adamantanecarboxylate)-6-O-α-D-galactopyranosyl-α-D-glucopyranose, heptakis (H-sulfate), heptasodium salt.

4. A method of inhibiting the complement system in a body fluid which comprises subjecting said body fluid to the action of an effective complement inhibiting amount of a compound selected from those of the formula:

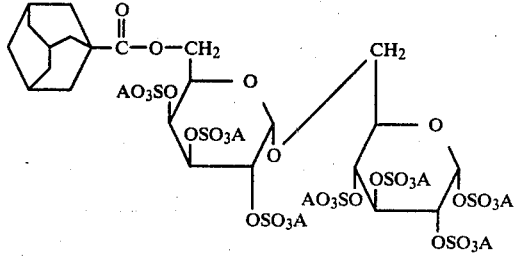

wherein A is a pharmaceutically acceptable cation salt, wherein the salt forming moiety is selected from the group consisting of alkali metal, alkaline earth metal, ammonia and substituted ammonia selected from the group consisting of trialkylamine ($C_1$–$C_6$), piperidine, pyrazine, alkanolamine ($C_2$–$C_6$) and cycloalkylamine ($C_3$–$C_6$).

5. A method of inhibiting the complement system in a warm-blooded animal which comprises administering to said warm-blooded animal an effective complement inhibiting amount of a compound selected from those of the formula:

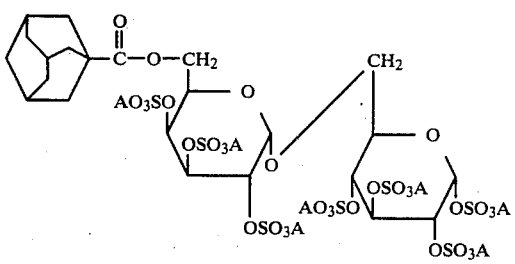

wherein A is a pharmaceutically acceptable cation salt, wherein the salt forming moiety is selected from the group consisting of alkali metal, alkaline earth metal, ammonia and substituted ammonia selected from the group consisting of trialkylamine ($C_1$–$C_6$), piperidine, pyrazine, alkanolamine ($C_2$–$C_6$) and cycloalkylamine ($C_3$–$C_6$).

6. The method according to claim 4 or 5, wherein the compound is 6'-(1-adamantanecarboxylate)-6-O-α-D-galactopyranosyl-α-D-glucopyranose, heptakis (H-sulfate), heptasalt with trimethylamine.

7. The method according to claim 4 or 5, wherein the compound is 6'-(1-adamantanecarboxylate)-6-O-α-D-galactopyranosyl-α-D-glucopyranose, heptakis (H-sulfate), heptasodium salt.

8. The method according to claim 5, wherein the compound is administered internally.

9. The method according to claim 5, wherein the compound is administered topically.

10. The method according to claim 5, wherein the compound is administered periodontally in the oral cavity.

11. The method according to claim 5, wherein the compound is administered intra-articularly.

12. The method according to claim 5, wherein the compound is administered parenterally.

13. A process for the preparation of a compound of the formula:

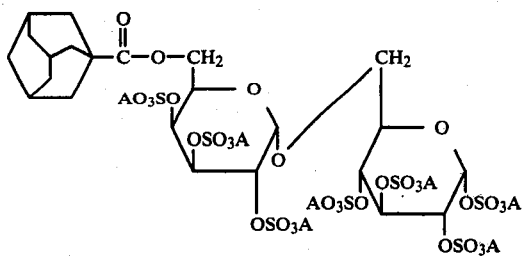

wherein A is a pharmaceutically acceptable cation salt, wherein the salt forming moiety is selected from the group consisting of alkali metal, alkaline earth metal, ammonia and substituted ammonia selected from the group consisting of trialkylamine ($C_1$–$C_6$), piperidine, pyrazine, alkanolamine ($C_2$–$C_6$) and cycloalkylamine ($C_3$–$C_6$), which comprises suspending 6-O-α-D-galactopyranosyl-α-D-glucopyranose in pyridine, adding calcium sulfate, heating at 75°–100° C. for 15–60 minutes, adding trityl chloride, heating and stirring for 2 hours, cooling, adding acetic anhydride, standing overnight, collecting solid 6-O-(6-O-trityl-α-D-galactopyranosyl)-α-D-glucopyranose, heptaacetate, heating with glacial acetic acid at 40°–70° C. for 4 hours, cooling and extracting with dichloromethane, evaporating extracts to a glass and purifying giving 6-O-α-D-galactopyranosyl-α-D-glucopyranose, heptaacetate, treating with 1-adamantoylchloride in pyridine with stirring for 20 hours, pouring into ice, giving 6′-(1-adamantanecarboxylate)-6-O-α-D-galactopyranosyl-α-D-glucopyranose, heptaacetate, dissolving in methanol:water:triethylamine (6:2:3), stirring for 24 hours and evaporating, giving 6′-(1-adamantanecarboxylate)-6-O-α-D-galactopyranosyl-α-D-glucopyranose, adding to a mixture of trimethylamine-sulfur trioxide in dimethylformamide and stirring for 24 hours, giving 6′-(1-adamantanecarboxylate)-6-O-α-D-galactopyranosyl-α-D-glucopyranose, heptakis (H-sulfate), heptasalt with trimethylamine and treating with an alkali metal or alkaline earth metal cation-containing compound or ammonia or a substituted ammonia other than trimethylamine selected from the group consisting of trialkylamine ($C_1$–$C_6$), piperidine, pyrazine, alkanolamine ($C_2$–$C_6$) and cycloalkylamine ($C_3$–$C_6$).

* * * * *